United States Patent [19]

Mehdizadeh et al.

[11] Patent Number: 4,623,835
[45] Date of Patent: Nov. 18, 1986

[54] WEB THICKNESS SENSOR USING LOOP-GAP RESONATOR

[75] Inventors: Mehrdad Mehdizadeh, Centerport, N.Y.; Wojciech Froncisz, Krakow, Poland; James S. Hyde, Dousman, Wis.

[73] Assignee: Medical College of Wisconsin, Inc., Milwaukee, Wis.

[21] Appl. No.: 589,641

[22] Filed: Mar. 14, 1984

[51] Int. Cl.[4] .................. G01B 7/02; G01R 33/08
[52] U.S. Cl. .................. 324/58.5 R; 324/58.5 C; 324/61 R; 324/316; 324/58.5 B; 333/219
[58] Field of Search .................. 333/219, 235; 73/159, 73/160; 324/58 R, 58 A, 58 B, 58 C, 58.5 R, 58.5 A, 58.5 B, 58.5 C, 316, 61 R

[56] References Cited

U.S. PATENT DOCUMENTS

| 3,514,703 | 5/1970 | Soga | 324/58.5 C |
| 4,435,680 | 3/1984 | Froncisz | 324/316 |
| 4,446,429 | 5/1984 | Froncisz | 324/316 |
| 4,504,788 | 3/1985 | Froncisz | 324/316 |

FOREIGN PATENT DOCUMENTS 1200275 7/1970 United Kingdom ........... 324/58.5 C

OTHER PUBLICATIONS

"Extrusion Web Thickness Sensors: Which is Right for Your Needs?", By Edward L. Sarber, Marketing Manager, Measurex Corp., Plastics Technology, Jun. 1983.

"Measurement Thickness + Basis Weight—Control Quality + Economy"—Lippke Microcomputer (Brochure) for Blown Film, Flat Film, Co-Extrusion and Coating.

"Gauge Systems and Interlayer Measuring in Co-Extrusion Blown-Cast Film and Sheeting", by Peter G. Mercer, Systems Development Engineer, Paul Lippke GmbH & Co. KG.

"On-Line Measurement & Control Systems for Continuous Process Lines"—Brochure by NDC.

"Magnetic Media Thickness Gauge and Control System—Model 7105", Brochure by NDC Systems.

"Measurex System 2002"—Brochure by Measurex, 1981.

Primary Examiner—Reinhard J. Eisenzopf
Assistant Examiner—Jose M. Solis
Attorney, Agent, or Firm—Barry E. Sammons

[57] ABSTRACT

The thickness of a web is measured by passing the web through the gaps of a loop-gap resonator. Changes in web thickness alter the resonant frequency of the resonator which is detected by a control circuit. Three embodiments of the invention are described, and in one embodiment, the moisture content of the web is also measured.

13 Claims, 15 Drawing Figures

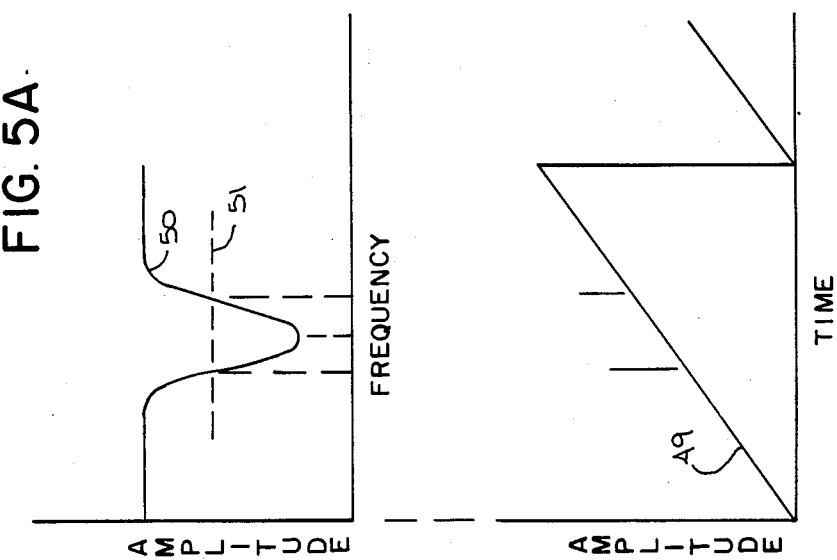
FIG. 5A.
FIG. 5B
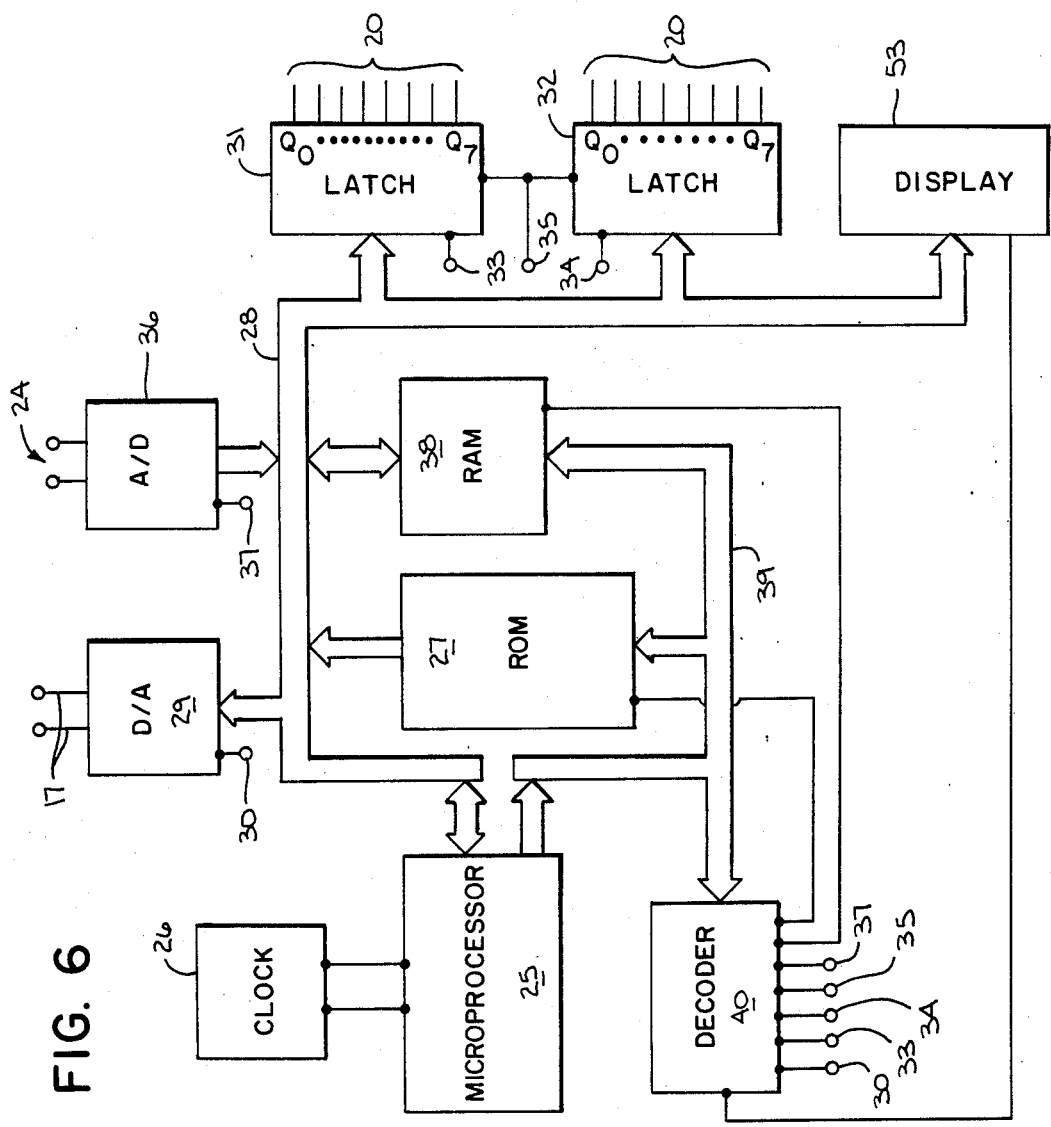
FIG. 6

WEB THICKNESS SENSOR USING LOOP-GAP RESONATOR

GOVERNMENT RIGHTS

The invention described herein was made in the course of work under a grant or award from the Department of Health and Human Services, GM27665. This invention was also made with Government support under PCM 8118976 awarded by the National Science Foundation. The Government has certain rights in this invention.

BACKGROUND OF THE INVENTION

The field of the invention is thickness sensors, and particularly sensors employed to measure the thickness of extruded webs.

To control the thickness of webs produced by an extrusion process a sensor capable of providing an accurate and reliable thickness feedback signal to the process control system must be provided. There are a number of such sensors available which employ a variety of technologies. These include: nuclear sensors which employ beta radiation; infrared sensors which employ electromagnetic waves at infrared frequencies; microwave sensors; laser sensors; x-ray sensors; and ultrasonic sensors. These sensors may operate by measuring the amount of radiation which is absorbed by the web, reflected by the web, or scattered by the web. No single sensor technology is suitable for all applications and the method which the sensor employs to make its measurement will usually depend on the nature of the web material and its thickness.

SUMMARY OF THE INVENTION

The present invention relates to a web thickness sensor which employs a loop-gap resonator and a resonance method to measure the thickness of dielectric materials. The sensor includes a loop formed in part by a conductive roller which supports the web to be measured and a shell which is spaced from the roller to form a pair of gaps through which the web passes. An oscillator is coupled to the loop and is operable to inject electromagnetic energy therein at the resonant frequency determined by the loop, the gaps and the dielectric constant of the web. The resonant frequency changes as a function of web thickness and a digital control system connects to the oscillator to sense the resonant frequency and provide a corresponding indication of web thickness.

A general object of the invention is to provide a sensitive web thickness sensor. The loop-gap resonator is neither a cavity resonator nor a conventional lumped circuit resonator. One of its characteristics, however, is that the gaps formed between its two sections function as the capacitive element and the electric field is concentrated in these gaps. Insertion of the dielectric web in the gaps perturbs the electric fields and results in a dramatic shift in resonant frequency. If the dielectric constant of the web is relatively uniform, the change in resonant frequency is a measurement of web thickness. Since frequency shifts are easily measured, a very sensitive instrument may be provided.

Another object of the invention is to measure the moisture content of a web material. Using the same instrument, the quality factor, or "Q", of the loop-gap resonator may be measured. At microwave frequencies the Q is dramatically affected by the moisture content of the web material, and hence, a sensitive measurement of moisture content is possible.

Another object of the invention is to measure the diameter of dielectric fibers. The same electric field which is produced in the gap, or gaps, of the loop-gap resonator may be employed to measure the diameter of dielectric fibers which are fed through the gap. In this instance it is preferable to feed the fiber through the gap in the direction of the longitudinal axis of the loop-gap resonator.

Yet another object of the invention is to measure the thickness of metal foils. The foil is fed through the gaps of the loop-gap resonator and it makes electrical contact with the conductive roller. The metal foil becomes an extension of the conductive roller, and variations in foil thickness become variations in the gap dimension, which are translated into easily measured changes in resonant frequency.

The foregoing and other objects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims herein for interpreting the scope of the invention.

BRIEF DESCRIPTION OF THE DRAWINGS

FIGS. 5a and 5b are graphs of signals which appear in the electronic circuitry of FIG. 4;

FIG. 6 is an electrical schematic diagram of the digital control system which forms part of FIG. 4;

DESCRIPTION OF THE PREFERRED EMBODIMENTS

Figure 1:
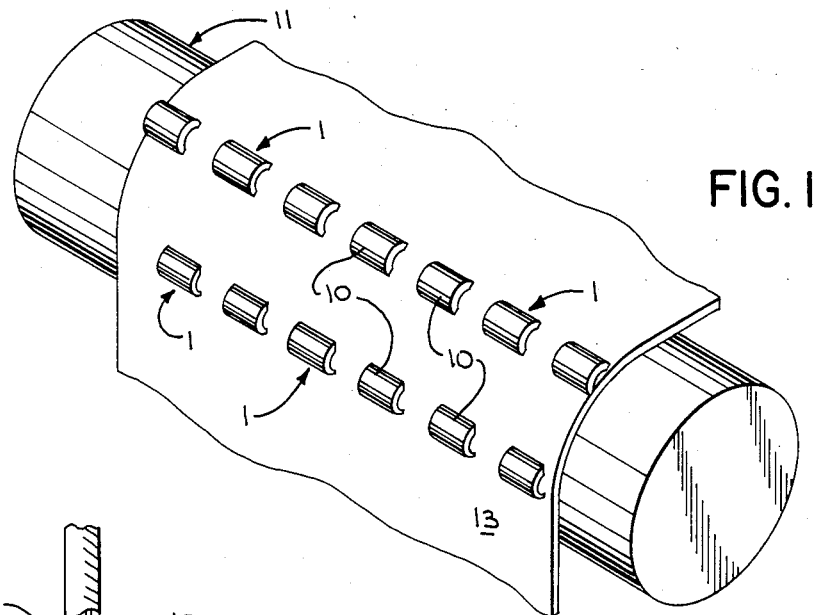
FIG. 1 is a partial perspective view of a first preferred embodiment of the thickness sensor.
Figure 2:
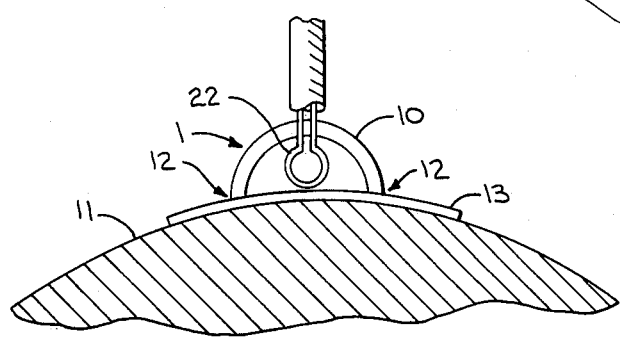
FIG. 2 is a view in cross section taken across the axis of rotation of the roller which forms part of FIG. 1.
Figure 3:
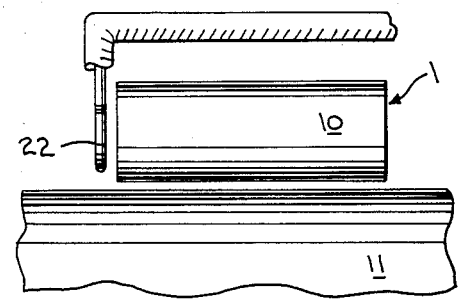
FIG. 3 is a partial elevation view of a single loop-gap resonator which forms part of FIG. 1.

Referring particularly to FIGS. 1-3, the first preferred embodiment of the invention employs a plurality of stationary loop-gap resonators 1 which are spaced across the width of the dielectric web material to be measured. Each loop-gap resonator 1 is formed by a cylindrical shell 10 which is supported over a metal roller 11 to present a pair of gaps 12 through which the web 13 passes. The shells 10 are arranged in two rows across the width of the web 13 with each successive shell 10 covering a small segment of the web width. By arranging the shells 10 in two rows, the entire lateral extent of the web surface can be measured without undue coupling between adjacent loop-gap resonators. As disclosed in U.S. Pat. No. 4,435,680 entitled "Microwave Resonator Structure", it is a characteristic of the loop-gap resonator 1 that its resonant frequency is not a function of its length. Thus, fewer, but longer, loop-gap resonators may be employed where low resolution is needed, or more, but shorter, loop-gap resonators 1 may be employed in high resolution applications.

The resonant frequency of each loop-gap resonator 1 is determined by the dimensions of the shell 10, its spacing from the roller 11, and the dielectric properties of the web material 13. It is a characteristic of the loop-gap resonator 1 that the electric field which it produces is concentrated in the gaps 12 through which the web material 13 is fed. The loop-gap resonator 1 is thus very sensitive to changes in the dimensions of these gaps 12 and to changes in the dielectric material fed through the gaps 12. The measurement method of the present invention assumes that the physical dimensions of the gaps 12 are maintained constant and that the dielectric constant of the web material 13 is relatively uniform. Under these circumstances, changes in the resonant frequency of the loop-gap resonator 1 is a direct measurement of changes in the thickness of the web material 13. For a complete description of the theory of operation of the loop-gap resonator 1, reference is made to co-pending U.S. patent application Ser. No. 310,231 which was filed on Oct. 9, 1981, and which is entitled "Microwave Resonator".

Referring to FIGS. 1-4, the resonant frequency of each loop gap resonator is measured by applying electromagnetic energy to each resonator 1 and monitoring the amplitude of the signal reflected back. The electromagnetic energy is produced by a voltage-controlled oscillator (VCO) 15 which generates a sinusoidal output signal on coaxial cable 16 at a frequency which is controlled by the level of an input signal on lines 17. This sinusoidal signal is applied through a microwave directional coupler 18 to the inputs of thirteen diode switches 19 (only four of which are shown in the drawings). Each diode switch 19 has a control lead 20 which is connected to TTL output ports on a digital control system 21, and when the control lead 20 is enabled, the diode switch 19 couples the microwave energy from the VCO 15 to an associated coupling loop 22. Each coupling loop 22 is positioned adjacent one end of a loop-gap resonator shell 10 where it couples with the magnetic field supported by the resonator. By controlling the diode switches 19, therefore, the microwave energy produced by the VCO 15 may be applied to any one of the thirteen loop-gap resonators 1.

At resonance the loop-gap resonator 1 reflects minimum energy back through the associated coupling loop 22 and diode switch 19. This reflected energy is diverted at the directional coupler 18 and applied to the input of an amplitude detector 23. The amplitude detector 23 converts the reflected microwave signal to a d.c. signal which is applied to an analog input port 24 on digital control system 21. As will now be described in more detail, the resonant frequency of each loop-gap resonator 1 is determined by sweeping the frequency produced by the VCO 15 through a pre-established range, and recording the frequency at which the reflected signal is at a minimum.

Referring particularly to FIG. 6, the digital control system is structured about an 8-bit microprocessor 25 which is driven by a clock 26. The microprocessor 25 operates in response to machine language program instructions stored in a read-only memory (ROM) 27 to write data to peripheral devices through an 8-bit data bus 28 and to read data from the data bus 28. One such peripheral device is a digital-to-analog converter (D/A) 29 which receives an 8-bit binary number from the data bus 28 when a control line 30 is enabled, and which produces a corresponding voltage level at output leads 17. As indicated previously, the voltage across the leads 17 controls the frequency produced by the VCO 15. With this structure the frequency applied to a loop-gap resonator 1 by the VCO 15 can be precisely controlled under the direction of the program instructions executed by the microprocessor 25.

The microprocessor 25 also writes data to a pair of latches 31 and 32 when respective control lines 33 and 34 are active. This data is coupled to the outputs of the latches 31 and 32 to drive the diode switch control lines 20 when a control line 35 is active. Any one of the thirteen diode switches 19 can be enabled in response to an appropriate program instruction executed by the microprocessor 25.

In response to instructions stored in the ROM 27, the microprocessor 25 reads the value of the reflected microwave signal applied to the analog input port 24. This analog input signal is converted to a binary number by an analog-to-digital converter (A/D) 36, and the microprocessor 25 reads this value when control line 37 is enabled. The value is stored in a random access memory (RAM) 38 where it is available for further analysis.

The elements of the digital control system 21 are enabled by address codes produced by the microprocessor 25 and applied to an address bus 39. These addresses are decoded by a decoder circuit 40 which enables the control line for the "addressed" device. The least significant bits of the address code are applied directly to the ROM 27 and RAM 38 to select a single 8-bit memory location therein.

Figure 4:
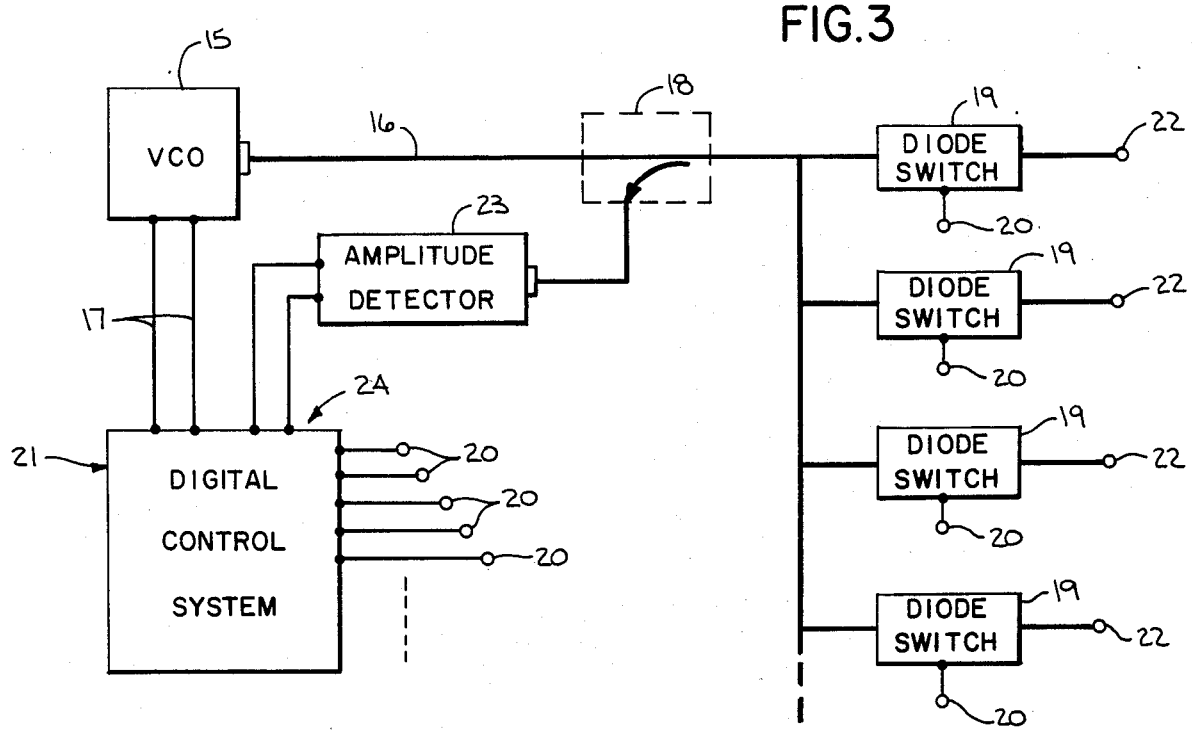
FIG. 4 is an electrical block diagram of the electronic circuitry employed with the thickness sensor of FIG. 1.

Referring particularly to FIGS. 4, 5, and 6, the digital control system 21 operates the VCO 15 and the diode switches 19 in a sequence of measurement cycles. The first step in each sequence is to enable one of the diode switches 19 by outputting the appropriate bit pattern to the latches 31 and 32. A measurement cycle is then performed in which a series of increasing numbers are written to the D/A converter 29 and the amplitude of the signals received at the A/D converter 36 are read and stored in the RAM 38. The "ramp" voltage which is applied to the VCO 15 during this measurement cycle is shown by the curve 49 in FIG. 5b, and the corresponding signal received at the input port 24 is shown in FIG. 5a by the curve 50. The curve 50 dips at the resonant frequency of the loop-gap resonator 1 which is energized, and this dip will shift in frequency as a function of web thickness. The exact resonant frequency is determined by looking up the stored values in the RAM 38 which match a preselected magnitude indicated by dashed line 51. These in turn are mapped to the corresponding two frequencies which produced the values and the resonant frequency is calculated as the midpoint between these two frequencies. The resonant frequency is then converted to a corresponding web thickness and this is output to a display 53 which connects to the data bus 28. The cycle is repeated for each loop-gap resonator to measure the thickness of the web 13 at successive locations across its width, and then the cycle is repeated.

It should be apparent that in the first preferred embodiment of the invention a plurality of stationary loop-gap resonators 1 are scanned electronically to provide thickness readings across the width of the web 13. In the second preferred embodiment now to be described a single loop-gap resonator is physically moved across the width of the web 13 using a different electronic circuit.

Figure 7:
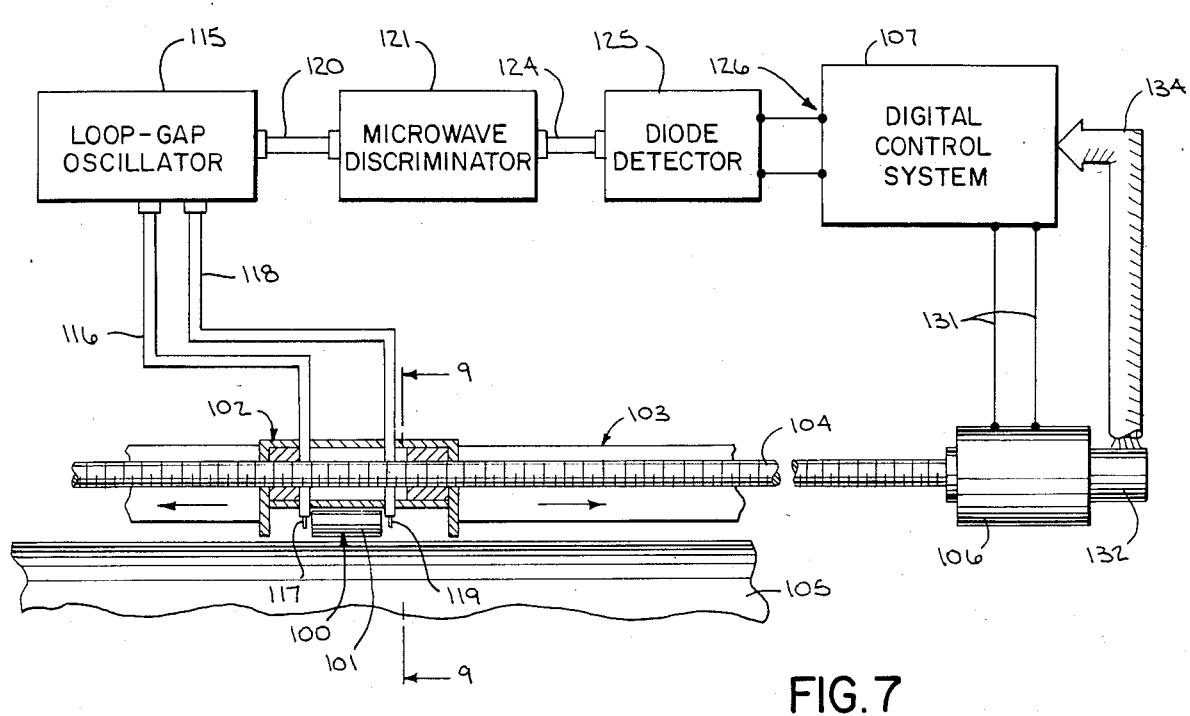
FIG. 7 is a schematic representation of a second embodiment of the thickness sensor.
Figure 9:
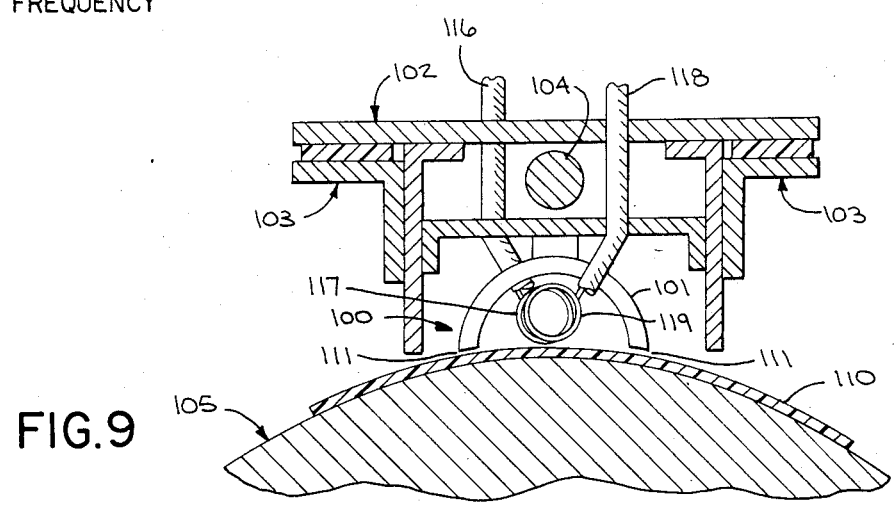
FIG. 9 is a view in cross section taken along the plane 9—9 indicated in FIG. 7.

Referring particularly to FIGS. 7 and 9, the second preferred embodiment of the invention includes a single loop-gap resonator 100 formed by a cylindrical shaped shell 101. The loop-gap resonator shell 101 is supported by a carriage 102 which is driven along a track 103 by a lead screw 104. The track 103 and associated lead screw 104 are supported above a metal roller 105 which carries the web material 110 to be measured. A d.c. electric motor 106 connects to one end of the lead screw 104, and it is operated by a digital control system 107 to rotate the lead screw 104 and move the carriage 102 from one end of the roller 105 to the other. The track 103 is precisely aligned with the axis of rotation of the roller 105 to maintain a constant spacing between the loop-gap resonator shell 101 and the metal roller 105 along its length.

As with the first embodiment of the invention, the shell 101 resonates at a frequency which is determined by its physical dimensions and the dimensions of the gaps 111 formed between it and the metal roller 110. This resonant frequency is altered by the dielectric characteristics of the web material 110, and if these characteristics are uniform throughout the web material 110, a change in the resonant frequency of the loop-gap resonator 100 is a measure of the change in web thickness.

Referring particularly to FIGS. 7 and 9, in contrast to the first embodiment of the invention in which a microwave oscillator is swept through a range of frequencies and the resonant frequency of the loop-gap resonator is measured, in the second embodiment, the loop-gap resonator 100 forms part of a loop-gap oscillator 115. In this self-oscillating detection system a microwave signal is applied through a coaxial cable 116 which is terminated by a coupling loop 117 positioned at one end of the loop-gap resonator 100. A signal is fed back to the loop-gap oscillator 115 through a second coaxial cable 118 which is terminated by a coupling loop 119 positioned at the other end of the loop-gap resonator 100. The frequency of the loop-gap oscillator 115 automatically changes to the resonant frequency of the loop-gap resonator 100 and produces a constant amplitude output signal of this frequency at coaxial cable 120. As the carriage is moved across the width of the web 110, therefore, changes in the web thickness appear as changes in the output frequency of the loop-gap oscillator 115.

Figure 8:
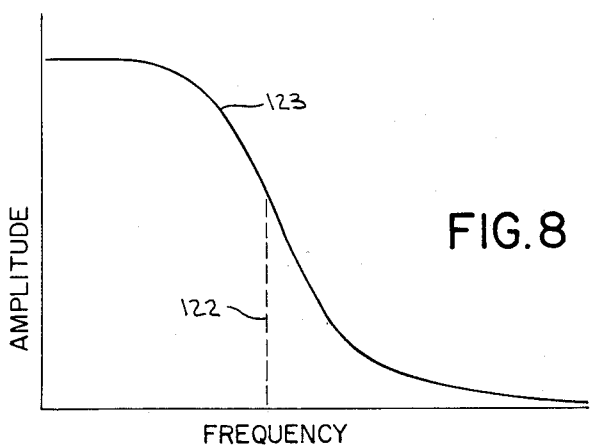
FIG. 8 is a graph of a signal which is produced in the sensor of FIG. 7.

Referring particularly to FIGS. 7 and 8, the output of the loop-gap oscillator 115 is applied to a microwave discriminator 121 which converts the variations in resonant frequency to corresponding changes in signal amplitude. The discriminator 121 is a low pass filter having its cut-off frequency adjusted to the output frequency range of the loop-gap oscillator 115. This transfer function is shown in FIG. 8, where the dashed line 122 indicates the output frequency of the loop-gap oscillator 115 when a web material 110 of typical thickness is being measured. As the web thickness changes, this frequency changes and the operating point moves up or down the sloped portion of the transfer function curve 123 to produce a corresponding output signal on coaxial cable 124. A diode detector 125 converts this microwave frequency signal to a d.c. signal having an amplitude which is inversely proportional to web thickness. This signal is applied to an analog input port 126 on the digital control system 107.

Figure 10:
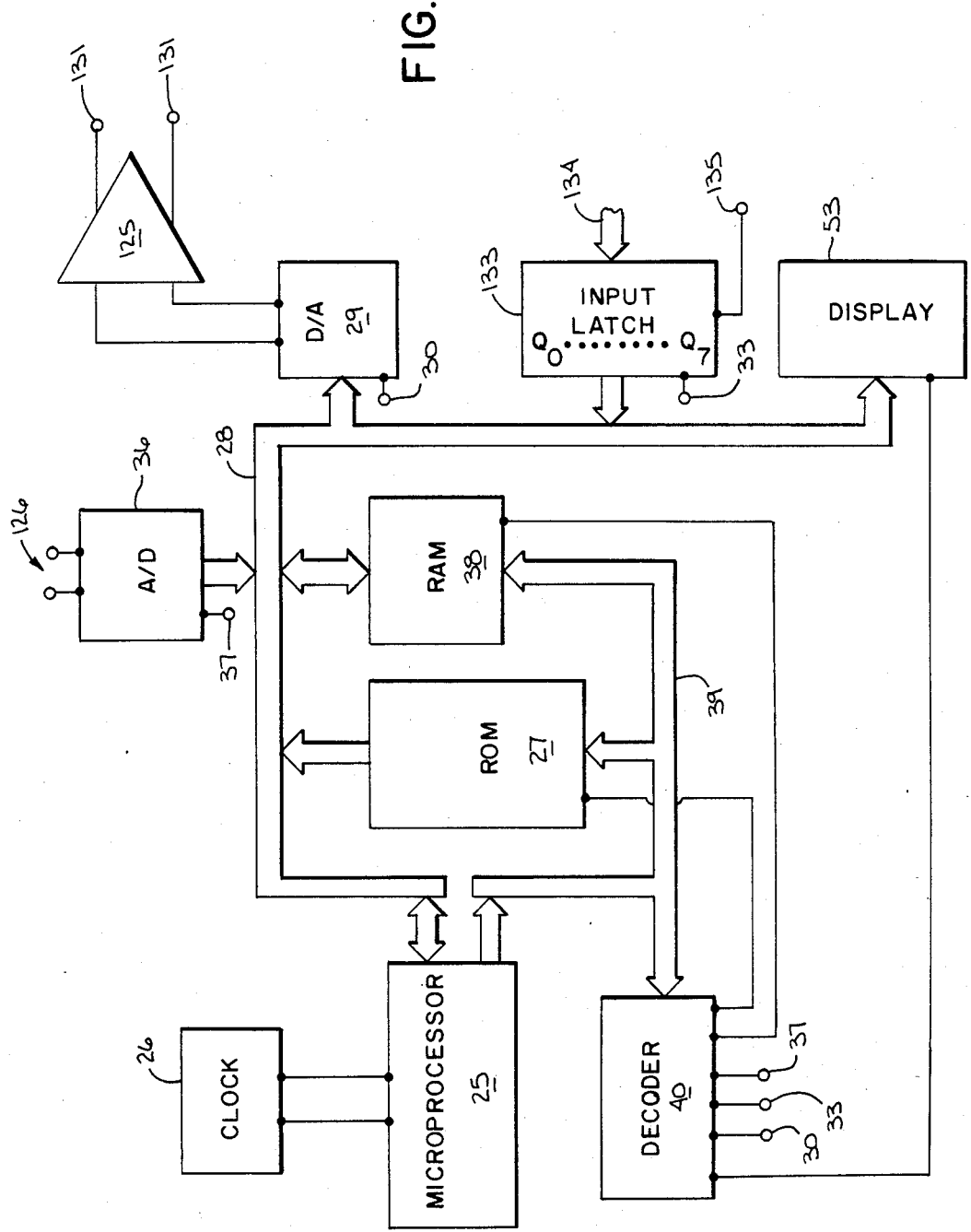
FIG. 10 is an electrical schematic diagram of the digital control system which forms part of FIG. 7.

Referring particularly to FIGS. 7 and 10, the digital control system 107 has many of the same elements as the control system 21 described above and shown in FIG. 6. These same elements are identified with the same reference numbers. In the control system 107, however, the A/D converter 36 receives the d.c. voltage from the diode detector 125 at the analog input port 126, and the D/A converter 29 outputs an analog velocity command to a servo amplifier 130 which drives the d.c. motor 106 through leads 131. In response to instructions stored in the ROM 27, the microprocessor 25 writes a velocity command number to the D/A converter 29 when the control line 30 is enabled, and this command is converted to a voltage which operates the d.c. motor 106 in the proper direction and at the desired speed. When the carriage 102 reaches either end of its scan across the width of the web 110, the motor 106 is decelerated to a stop and then accelerated in the opposite direction to repeat the scanning cycle.

The position of the carriage 102 is continuously monitored by a shaft encoder 132 which is mounted to the shaft of the d.c. motor 106. The shaft encoder 132 is an absolute position feedback device which applies an 8-bit position code to an input latch 133 through a cable 134. Each time the encoder 132 indicates an increment of position change, it clocks the input latch 133 through a control line 135. The microprocessor 25 may read the current position of the carriage 102 by enabling control line 33 and reading the contents of the input latch 133.

A measurement cycle is comprised of a series of thickness readings which are made as the loop-gap resonator 100 is moved across the width of the web 110. Such a thickness reading is made by inputting the digitized voltage received at the analog input port 126 and mapping this reading to a corresponding web thickness. These thickness readings are matched up with position information which is read from the input latch 133 and a thickness profile is formed for output to the display 53. Preferably, a number of thickness measurements are made at each discrete position indicated by the signal from the shaft encoder 132. Any readings which deviate significantly from the average are discarded and an average thickness is calculated from the remaining thickness readings. This averaging filters out noise produced by mechanical vibrations of the machine.

In both preferred embodiments described above the thickness of insulating materials is measured by sensing the change in dielectric properties in the gaps of the loop-gap resonator. It is also possible, in some instances, to measure the thickness of electrically conductive sheet materials, such as metal foils. In such measurements the metal foil is draWn over the roller, beneath the cylindrical shell of the loop-gap resonator as described above. However, in this instance the metal foil forms part of the loop-gap resonator and the thickness of the metal foil determines the spacing in the two gaps. Since the resonant frequency of the loop gap resonator is a function of the dimensions of its gaps, the resonant frequency can be used as a measure of metal foil thickness.

In both of the above measurement methods it is assumed that the spacing between the cylindrical shell of the loop-gap resonator and the associated metal roller is constant. In practice this is not economically possible to obtain. Instead, it is easier to calibrate the system by making measurements across the width of the roller with no web material in place. These calibration measurements are employed to calculate an array of offset values which are stored in the RAM 38 of the control system. When the web material is subsequently measured, these stored offset values are used to correct the readings taken at corresponding points across the width of the roller.

A similar technique can also be used to calibrate the measurement system for errors produced by variations in the radius, or "roundness" of the roller. In such case, an additional position transducer is coupled to the roller shaft and the roller orientation is sensed and input to the digital control system through an additional 8-bit input latch. A two-dimensional array of offset values are thus produced and stored during the calibration cycle. The proper offset to be applied during the measurement cycle is read from this stored array using the current position along the length of the roller and the current rotational orientation of the roller as indexes.

Figure 11:
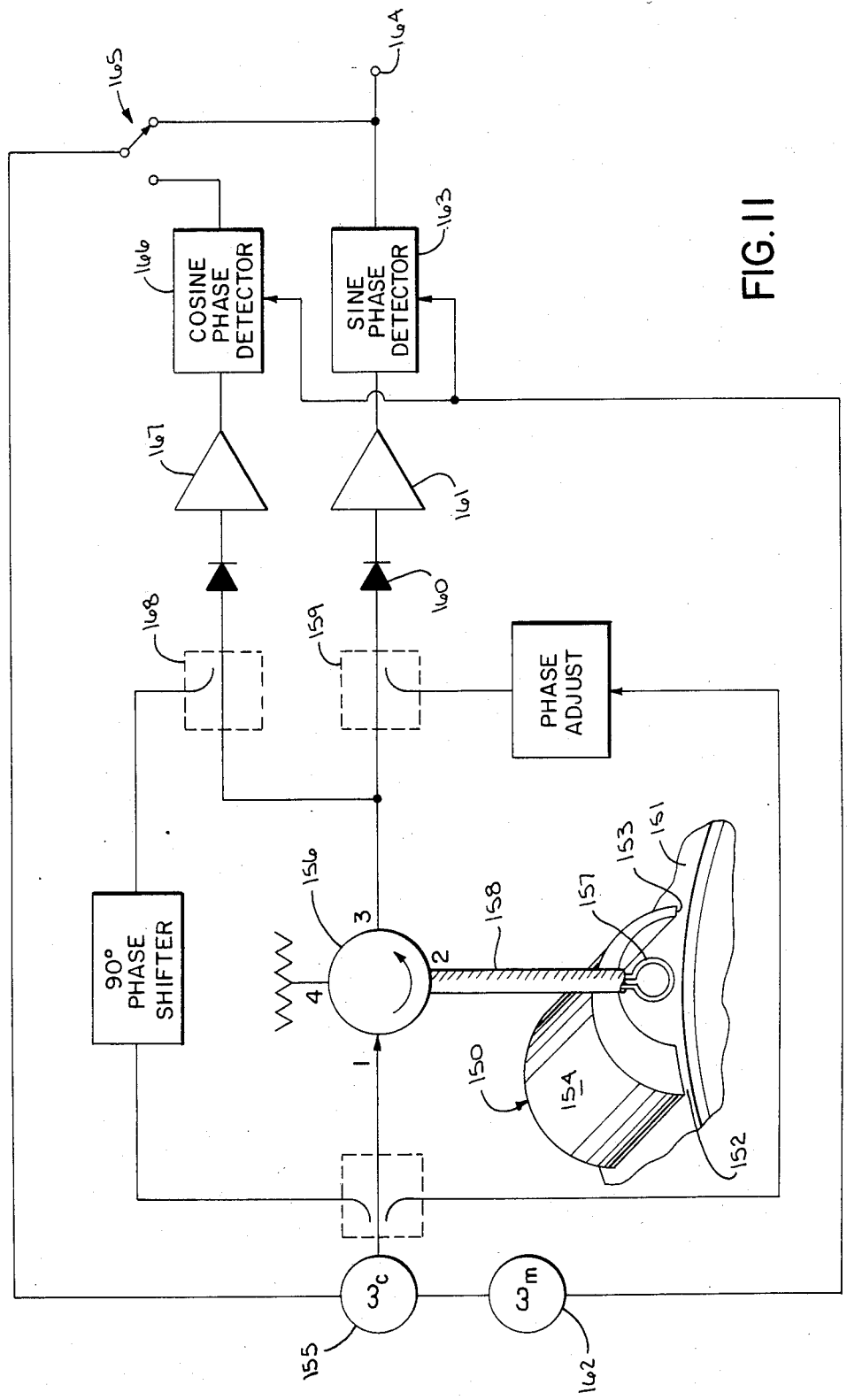
FIG. 11 is a schematic drawing of a third embodiment of the thickness sensor.

Yet another embodiment of the invention is disclosed in FIG. 11. In this third embodiment a microwave bridge is employed to detect the shift in frequency of a loop-gap resonator 150 and to provide additional information regarding a web 151 which passes through its gaps 152 and 153. In this embodiment, however, the wall thickness of the cylindrical shell 154 varies significantly to provide one gap 152 with a substantially larger surface area than that of the other gap 153. The resonant frequency of the loop-gap resonator 150 is determined by the capacitance of these gaps:

$$v = (1/LC)^{\frac{1}{2}}/2\pi$$

where:
$C = C_1 C_2 / (C_1 + C_2)$
$C_1 = \epsilon w_1 Z / t$ = capacitance of gap 152
$C_2 = \epsilon w_2 Z / t$ = capacitance of gap 153
and where:
$w_1$ = width of gap 152 $>>$ $w_2$ = width of gap 153
then:
$C \simeq \epsilon w_2 Z / t$
$v \simeq (t/L\epsilon w_2 Z)^{\frac{1}{2}}/2\pi$ In other words, the resonant frequency of the loop-gap resonator 150 is determined primarily by the physical dimensions and dielectric properties of the gap 153, and it is relatively insensitive to changes in the gap 152. The microwave signal reflected from the loop-gap resonator 150 is thus a measure of web thickness in the gap 153 with very little interference from signals produced as a result of variations in the gap 152.

The microwave bridge circuit in FIG. 11 provides information beyond that which can be provided by the first two embodiments described above. The microwave bridge circuit includes a voltage controlled microwave oscillator 155 which applies a microWave signal to port 1 of a circulator 156. This signal is applied to the loop-gap resonator 150 by a coupling loop 157 which connects to port 2 of the circulator 156 through coaxial cable 158. The microwave signal reflected from the loop-gap resonator 150 is circulated to port 3 on the circulator 156 where it is applied through a directional coupler 159 to a detector diode 160.

The reflected microwave signal is mixed with a reference microwave signal in the directional coupler 159, and the resulting difference signal is rectified by the detector diode 160 and amplified at 161. This demodulated signal has a frequency $\omega_m$ which is determined by a frequency modulation oscillator 162 that connects to the microwave oscillator 155. This same frequency modulation signal is applied to the reference input on a sine phase detector 163. The demodulated microwave signal is applied to the input of the sine phase detector 163 and an output signal is produced at terminal 164 which has an amplitude proportional to the in-phase component of the microwave signal reflected from the loop-gap resonator 150.

A switch 165 connects to the output 164, and when it is set to the "absorption" mode as shown in FIG. 11, the output signal is fed back to the control input on the voltage controlled oscillator 155. This feedback signal locks the voltage controlled oscillator 155 to the resonant frequency of the loop-gap resonator causing it to track any variations due to web thickness. In this absorption mode of operation, the amplitude of the second harmonic of this signal at the output 164 is a measure of the quality factor, or "Q", of the loop-gap resonator 150. Since quality factor is altered substantially by water at microwave frequencies, the output signal in the absorbtion mode is also a measure of the moisture content of the web 151.

When the switch 165 is changed to a "dispersion" mode, the signal which is fed back to the voltage controlled oscillator 155 is produced by a cosine phase detector 166. The cosine phase detector 166 is driven by an amplifier 167 which receives the reflected microwave signal from the loop-gap resonator 150 after it is mixed with a 90 degree phase-shifted reference signal in a directional coupler 168. As a result, the output of the cosine phase detector 166 has an amplitude which is proportional to the out-of-phase component of the microwave signal reflected from the loop-gap resonator 150. The signal which is produced simultaneously at the output 164 of the sine phase detector 163 now changes as a function of resonant frequency. When in this dispersion mode of operation, therefore, the system measures web thickness.

It should be apparent from the above description that by merely switching between the two moles of operation, the system of FIG. 11 will measure both web thickness and moisture content. In addition, by performing a noise analysis on the output signal it is possible to determine the spatial distributions of imperfections in the web 151. Various types of known automatic frequency circuits (AFC) may be employed to tune the oscillator 155 to the "average" resonant frequency of the loop-gap resonator 150. The time over which the average resonant frequency is determined will depend on the velocity of the web 151.

Figure 12:
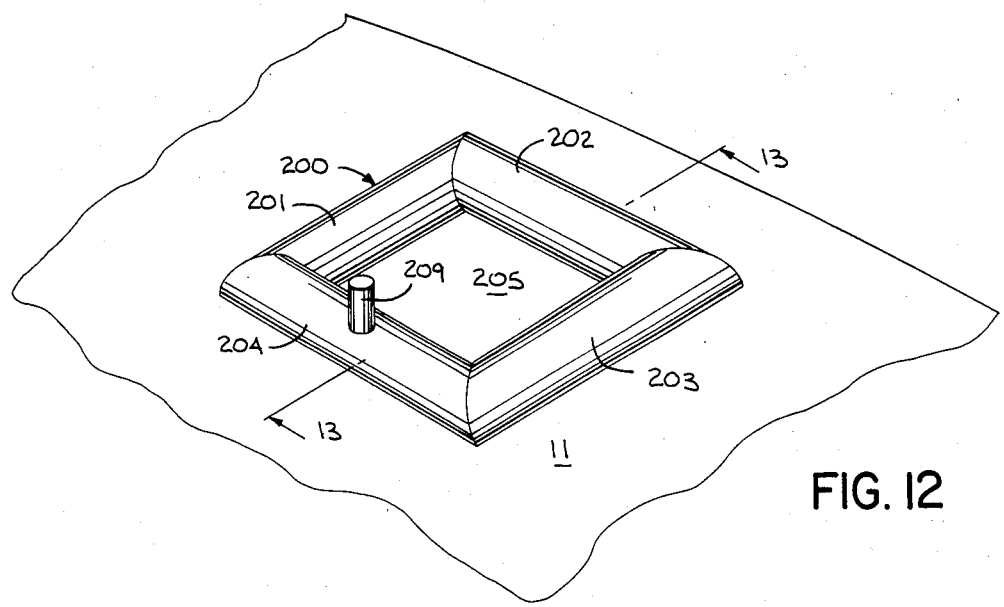
FIG. 12 is a partial perspective view of a fourth embodiment of the invention.
Figure 13:
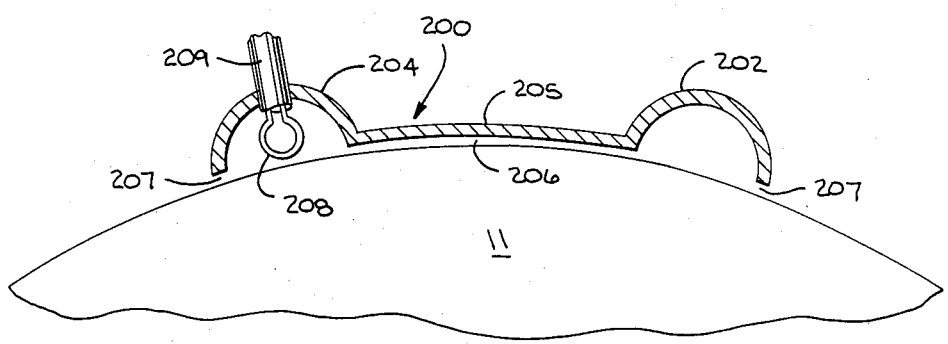
FIG. 13 is a view in cross section taken through the plane 13—13 in FIG. 12.

In all of the above embodiments of the invention the loop-gap resonator is formed by a straight shell which is open at each of its ends. The return path for the magnetic flux in such structures is outside the confines of the shell. An alternative loop-gap resonator structure which provides a confined return path for the magnetic flux is shown in FIGS. 12 and 13. A complete description of the manner in which this resonator operates is provided in co-pending U.S. patent application Ser. No. 414,642 which was filed on Sept. 3, 1982, and is entitled "Enclosed Loop-Gap Resonator". The shell 200 is comprised of four straight segments 201, 202, 203 and 204 which are linked together to form an enclosed rectangle. The center of the rectangle is a solid plate 205 which connects to the inner edge of each segment 201–204.

As shown best in FIG. 13, the shell 200 has a gap 207 which extends around its entire periphery and a gap 206 formed between the plate 205 and the conductive roller 11. Electromagnetic energy is introduced into the resulting enclosed loop-gap resonator by a coupling loop 208 formed at the end of a coaxial cable 209. The magnetic flux is confined to the enclosed loop formed by the segments 201–204 and the electric field is confined to the gaps 206 and 207. The resonant frequency of this structure will vary as a function of the dielectric properties of a web (not shown) which is fed over the roller 11 and into the gaps 206 and 207. Numerous other enclosed loop-gap geometries are also possible as suggested in the above-cited U.S. patent application Ser. No. 414,642.

Figure 14:
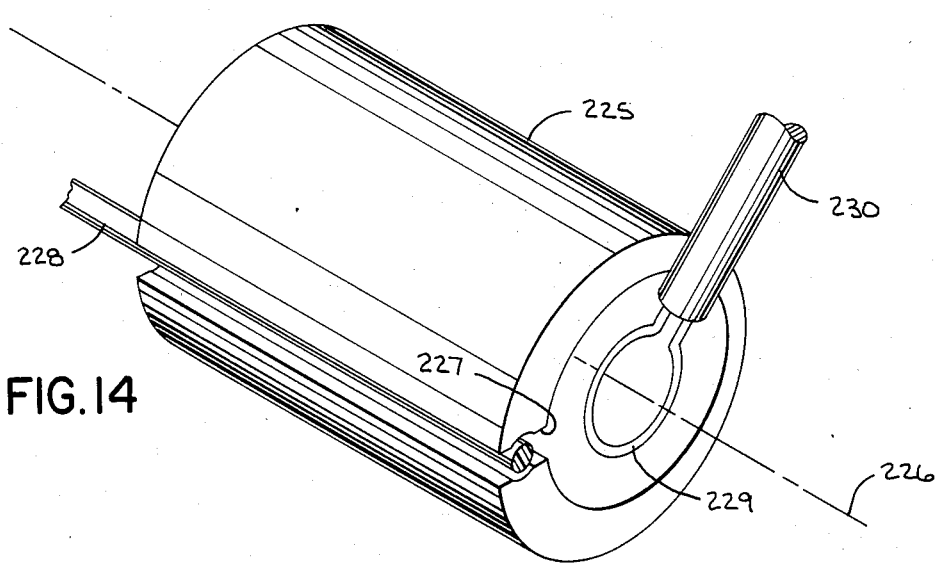
FIG. 14 is a perspective view of a fifth embodiment of the invention which is employed to measure fiber diameter.

Referring particularly to FIG. 14, another structure which employs the measurement method of the present invention is shown. In this embodiment the loop-gap resonator is formed as a conductive loop 225 around a central longitudinal axis 226. A single gap 227 is formed in the loop 225 along its entire longitudinal length, and a dielectric filament 228 is fed through this gap 227 in the lengthwise direction. Electromagnetic energy is coupled to the loop-gap resonator 225 through a coupling loop 229 formed at the end of a coaxial cable 230. The loop-gap resonator will resonate at a frequency which is determined by the diameter of the loop 225, the dimensions of the gap 227 and the dielectric properties of the filament. As with the measurement of webs, if the dielectric properties of the filament are relatively uniform, the resonant frequency of the loop-gap resonator is a measure of the size, or diameter, of the filament 228. Any of the electric control systems described above may be employed in this structure.

We claim:

1. A method for measuring the thickness of a material, the steps comprising:
   forming a loop-gap resonator having a gap across which an electric field is established;
   feeding the material to be measured through the gap;
   measuring the resonant frequency of the loop-gap resonator; and
   converting the measured resonant frequency to a thickness dimension.

2. The method as recited in claim 1 in which the resonant frequency of the loop-gap resonator is measured by applying electromagnetic energy to the loop-gap resonator, measuring the amplitude of the electromagnetic energy reflected back from the loop-gap resonator, and adjusting the frequency of the applied electromagnetic energy until resonance is found.

3. The method as recited in claim 1 in which the loop-gap resonator is formed by two separate elements which provide a pair of gaps that each support an electric field, and the material to be measured is fed through both gaps.

4. A web thickness sensor, the combination comprising:
   a loop-gap resonator formed by two conductive elements which are spaced apart to provide a pair of gaps;
   first means for feeding the web through the gaps of the loop-gap resonator;
   second means for applying electromagnetic energy to the loop-gap resonator to produce an electric field across each gap;
   third means coupled to the second means for measuring the resonant frequency of the loop-gap resonator as the web is fed through the loop-gap resonator gaps; and
   fourth means coupled to the third means for converting the resonant frequency measurements to web thickness data.

5. The web thickness sensor as recited in claim 4 in which one of the conductive elements of the loop-gap resonator is a metal roller which supports the web and the other conductive element is a shell which is spaced from the metal roller.

6. The web thickness sensor as recited in claim 5 in which the shell is shaped to provide one of said gaps with an effective area substantially greater than the effective area of the other of said gaps.

7. The web thickness sensor as recited in claim 5 which includes:
   a carriage which supports the shell and is slidably mounted to a track which extends along the length of the metal roller; and
   drive means for moving the carriage along the track to measure the thickness of the web across its entire width.

8. The web thickness sensor as recited in claim 5 in which there are a plurality of shells disposed along the length of the metal roller to form a corresponding number of separate loop-gap resonators, and the second means for applying electromagnetic energy to the loop-gap resonator includes switch means for applying the electromagnetic energy to each of the separate loop-gap resonators in sequence to thereby measure the thickness of the web at discrete positions across the width of the web.

9. A web thickness sensor which comprises:
   a metal roller for supporting the web as it is fed over the roller;
   a loop-gap resonator formed by a cylindrical shell which is mounted in spaced relation to the metal roller to define a pair of gaps through which the web is fed;
   a coupling loop mounted in fixed relation to the shell;
   means for applying high frequency electromagnetic energy to the loop-gap resonator through the coupling loop;
   means for determining the resonant frequency of the loop-gap resonator by measuring the electromagnetic energy reflected back from the loop-gap resonator; and
   means for calculating the web thickness from such measurement.

10. The web thickness sensor as recited in claim 9 in which the resonant frequency of the loop-gap resonator is in the microwave region of the spectrum.

11. The web thickness sensor as recited in claim 9 in which the means for calculating web thickness includes means for determining the resonant frequency of the loop-gap resonator when no web is placed in the gaps and means for storing an offset value which is employed to correct the resonance measurement.

12. A web thickness sensor, the combination comprising:
   an enclosed loop-gap resonator formed by a conductive shell which closes on itself and a conductive roller which is spaced from the conductive shell to form an outer gap and an inner gap therebetween;

first means for applying electromagnetic energy to the enclosed loop-gap resonator to produce an electric field across each of said inner and outer gaps;

second means coupled to the first means for measuring the resonant frequency of the enclosed loop-gap resonator as the web is fed through its gaps; and third means coupled to the second means for converting the resonant frequency measurements to web thickness data.

13. A filament size sensor, the combination comprising:

a loop-gap resonator formed from an electrically conductive material and being disposed around a central longitudinal axis, said loop-gap resonator having a length in the direction of the central longitudinal axis and a gap formed along the length;

first means for applying electromagnetic energy to the loop-gap resonator to produce an electric field across the gap;

second means coupled to the first means for measuring the resonant frequency of the loop-gap resonator as the filament is fed through the gap in the direction of the central longitudinal axis; and third means coupled to the second means for converting the resonant frequency measurements to filament size data.

* * * * *